United States Patent [19]

Chamuel

[11] Patent Number: 4,593,565
[45] Date of Patent: Jun. 10, 1986

[54] APPARATUS FOR NONDESTRUCTIVE WORKPIECE INSPECTION EMPLOYING THERMOELASTICALLY AND ELECTRODYNAMICALLY INDUCED ELASTIC WAVES

[75] Inventor: Jacques R. Chamuel, Framingham, Mass.

[73] Assignee: The Charles Stark Draper Laboratory, Inc., Cambridge, Mass.

[21] Appl. No.: 521,325

[22] Filed: Aug. 8, 1983

[51] Int. Cl.⁴ ............................................. G01N 29/04
[52] U.S. Cl. ....................... 73/601; 73/632; 73/643; 73/627
[58] Field of Search ............... 73/587, 601, 632, 801, 73/643, 627

[56] References Cited

U.S. PATENT DOCUMENTS

| 4,267,732 | 5/1981 | Quate | 73/606 |
| 4,338,822 | 7/1982 | Yamaguchi et al. | 73/643 |
| 4,385,634 | 5/1983 | Bowes | 73/643 |

OTHER PUBLICATIONS

"20-MHz Acoustic Waves from Pulsed Thermoelastic Expansions of Constrained Surfaces", von Gutfeld et al., *Applied Physics Letters*, vol. 30, No. 6, Mar. 15, 1977, pp. 257-259.
"Experiments on Some Electrodynamic Ultrasonic Vibrators", Barone et al., *Acustica*, vol. 4 (1954), pp. 182-184.
"Generation of Elastic Waves by Transient Surface Heating", White, *Journal of Applied Physics*, vol. 34, No. 12, Dec. 1963, pp. 3559-3567.

*Primary Examiner*—Howard A. Birmiel
*Attorney, Agent, or Firm*—Weingarten, Schurgin, Gagnebin & Hayes

[57] ABSTRACT

Method and apparatus for nondestructive inspection and detection of flaws in a workpiece according to four techniques is disclosed. Elastic waves are thermoelastically or electrodynamically induced in a workpiece by electric current energization of an elastic wave inducing source adapted to be disposed in contact with the workpiece remote from a defect. An acoustic sensor is disposed in elastic wave transmitting contact with the workpiece remote from the source and produces an output signal having an amplitude representative of received elastic waves. The presence of a crack, flaw or defect in the workpiece is detectable as a variation in the amplitude or other characteristics of the acoustic sensor output signal.

24 Claims, 6 Drawing Figures

FORM OF SOURCE AND RECEIVER
(LESS SENSITIVE TO ELECTROMAGNETIC NOISE)

APPARATUS FOR NONDESTRUCTIVE WORKPIECE INSPECTION EMPLOYING THERMOELASTICALLY AND ELECTRODYNAMICALLY INDUCED ELASTIC WAVES

FIELD OF THE INVENTION

This invention relates to generation and detection of stress waves in materials, to nondestructive testing techniques and more specifically to a nondestructive testing technique employing thermoelastically and electrodynamically induced elastic waves.

BACKGROUND OF THE INVENTION

It is of particular import to be able to determine the presence of a defect via nondestructive testing means in many applications. In manufacturing processes, the ability to perform nondestructive testing of manufactured articles avoids waste and costs associated with destructive testing. Moreover, destructive testing of components only provides statistical probabilities of component integrity for actual articles shipped since it is apparent that when destructive testing is employed, only non-tested articles are delivered to a customer. The ability to perform nondestructive testing provides the option of testing all manufactured articles yielding such benefits as improved product integrity and greater customer satisfaction.

Of present interest are nondestructive test techniques employing acoustic emission analysis of a workpiece under test. Typically, elastic waves are either induced in a workpiece or are inherent in a particular process. Elastic waves in a workpiece may interact with a defect to produce a change in an output signal from an acoustic sensor in elastic wave transmitting contact with the workpiece.

One method and apparatus for inspection of ceramic parts, and more specifically posistors, is disclosed in U.S. Pat. No. 4,277,977 to Lubitz, et al. Lubitz discloses that a voltage may be applied to a ceramic element and that, as a consequence of the applied voltage, temperature oscillation will occur in the vicinity of a pre-existing defect producing acoustic or sound pulses due to oscillatory abrasion of defect or fissure surfaces. The acoustic or sound pulses are detected via acoustic emission analysis techniques to produce an output signal indicative of the presence of the defect.

U.S. Pat. No. 4,086,817 to Jon, et al. recites a method and apparatus applicable for determination of weld integrity employing acoustic emission analysis. During AC welding operations, stress waves are generated and are emitted during time periods when the AC power is on, during a post-weld time period and during a third time period comprised of all the time intervals in which the absolute magnitude of each of the energy pulses is decaying. By analyzing acoustic emissions corresponding to stress waves emanating from the weld site, the integrity of the weld site may be ascertained.

Co-filed application Ser. No. 518528, of the same inventor and assignee as the present invention discloses a probe for inducing elastic waves in a workpiece and producing an output signal indicative of a defect.

SUMMARY OF THE INVENTION

In accordance with the present invention it is disclosed that thermoelastically and electrodynamically induced elastic waves may be generated in a workpiece by current pulse, current pulse code, current burst, or continuous current modulation energization of an elastic wave source. An acoustic wave sensor is disposed in contact with the workpiece and is operative to produce an output signal representative of received elastic waves.

In one embodiment of the invention elastic waves are induced in a conductive workpiece by applying a point contact electrode to the workpiece and providing a large area workpiece contact as a path for return current. A pulse generator is connected to the electrode and to the large area contact. Upon pulse energization of the electrode, elastic waves are induced in the conductive material due to the thermoelastic effect resulting from material heating and consequent expansion and contraction of the material in the vicinity of the electrode point contact where high current density and large local heating transients occur. an acoustic sensor is disposed in contact with the workpiece and is operative to produce an output signal having an amplitude representative of received elastic waves at the acoustic sensor. A resistive current path through the workpiece may be similarly excited as an acoustic source from the thermal expansion of the current path material. The presence of a crack or fissure in the workpiece is detectable as a variation in the acoustic sensor output signal.

Another embodiment of the invention is applicable for inspection of workpieces of nonconductive or conductive material. A fine wire is disposed in a nonconductive workpiece, is wrapped tightly around the workpiece, or otherwise affixed to the workpiece in an acoustically conducting manner with ends of the wire connected to a pulse generator. Upon pulse activation of the wire, local heating of the wire produces elastic waves by thermoelastic effect of the wire or adjacent material which are transmitted to and detected by an acoustic sensor disposed in elastic wave transmitting contact with the workpiece.

Additionally, a wire scanning magnet may be disposed adjacent the fixed wire bonded to large surface areas. Pulse energization of the wire in proximity to the magnet causes enhanced elastic wave inducement in the workpiece due to the electrodynamic effect of pulse current flow along the wire path within the field of the magnet. Same fixed-coil scanning magnet concept may be used as a receiver to detect flaws in large surface areas.

DESCRIPTION OF THE DRAWINGS

The invention will be more fully understood from the following description taken in conjunction with the accompanying drawings, in which.

DETAILED DESCRIPTION OF THE INVENTION

In accordance with the present invention there is disclosed a method and apparatus for nondestructive inspection of a workpiece in which elastic waves are induced in the workpiece by thermoelastic or electrodynamic effect and an acoustic sensor is disposed in contact with the workpiece to produce an output signal representative of received elastic waves. Various embodiments of the invention permit nondestructive inspection of workpieces fabricated of conductive and nonconductive materials.

Figure 1:
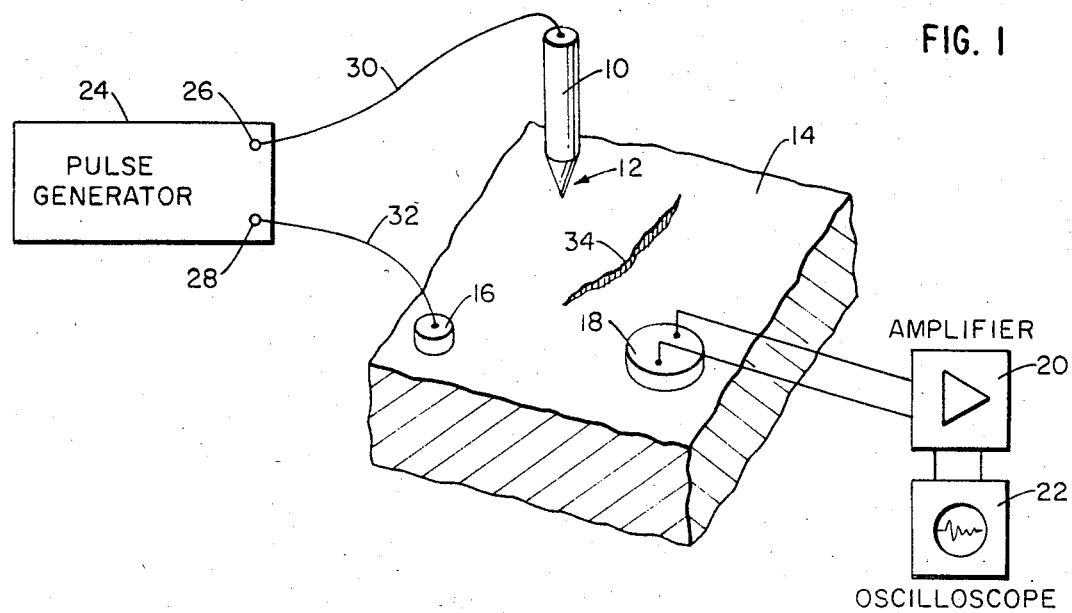
FIG. 1 illustrates an embodiment of the present invention intended for nondestructive inspection of workpieces fabricated of a conductive material.

Referring to FIG. 1, an electrode 10 which tapers to a point 12 contacts a workpiece 14 of conductive material. The electrode 10 may be a conductive rod which tapers to a point, a ball electrode, or any other suitable structure providing a point contact with the workpiece 14. An electrode 16 having a large contact area is applied to the workpiece 14 a specified distance from the electrode point 12. An acoustic wave sensor 18 is disposed in elastic wave transmitting contact with the workpiece 14 at a third location and is operative to produce an electrical output signal representative of elastic waves received at that third location. The sensor 18 may be a piezoelectric sensor, a fiber optic, acoustically modulated sensor, a capacitive sensor, or any other suitable acoustic sensor. The output signal from the acoustic wave sensor 18 is applied to an amplifier 20. The amplifier output signal may be applied to an oscilloscope 22 for real time analysis or to any form of recorder or instrumentation to permit analysis of received signals at a later time.

A pulse generator 24 has output 26 and 28 electrically connected capacity to the point contact electrode 10 and large contact area electrode 16 via respective wires 30 and 32 of suitable current capacity. Elastic waves are induced in the workpiece 14 by current pulse heating in the vicinity of the contact point of the electrode 10. For this purpose, an electrical pulse of predetermined current is transmitted through the wire 30 to the electrode 10. The current pulse passes through the tapered point 12 of the electrode 10 to the conductive material 14 and through the conductive material 14 along a current return path to the large contact area electrode 16 and through the return wire 32. As a consequence of the point contact of the electrode 10 with the conductive material 14, rapid heating occurs at the location of the contact point 12 between the electrode 10 and the conductive workpiece 14, due to the high current density at the point 12. Elastic waves are thus thermally induced in the conductive workpiece 14.

In the absence of a defect or flaw, elastic waves travel through the workpiece 14 to the acoustic wave sensor 18 to produce an output signal having an amplitude and waveform representative of diverse characteristics of the material and shape of workpiece 14. The initial portion of that output signal will reflect the direct transmission of the acoustic wave through the workpiece 14 and is the signal of interest in general. Subsequent signal waveforms are a complex function of wave reflections, etc. The acoustic sensor 18 and amplifier 20 produce an output signal typically for display on an oscilloscope 22 or application to other signal processing circuitry. The presence of a defect 34 in the conductive workpiece 14, produces a variation in the amplitude of the acoustic sensor 18 output signal which may be a diminished output signal, an amplified output signal, or an otherwise altered output signal depending on the nature and location of the defect 34. A resistive current path through the workpiece or material 14 can be utilized as an acoustic generator in the same manner.

Figure 2:
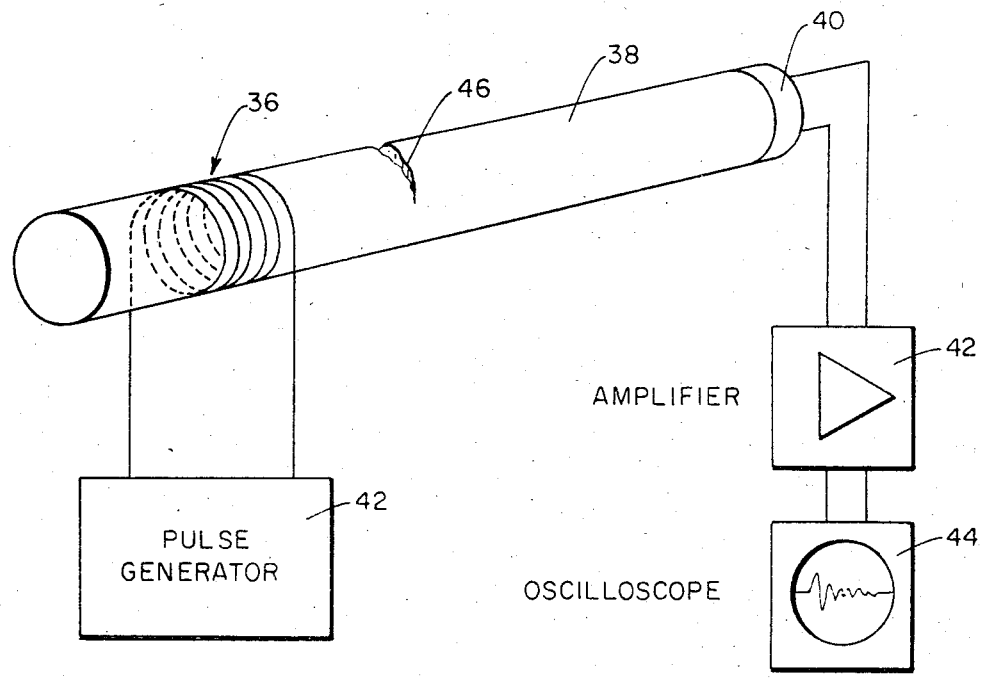
FIG. 2 illustrates an embodiment of the present invention for nondestructive inspection of nonconductive workpieces in which a coil is tightly wrapped around the workpiece.

In another embodiment of the invention illustrated in FIG. 2, a coil 36 is tightly wrapped around and in physical contact with a nonconductive workpiece 38. An acoustic wave sensor 40 is disposed in elastic wave transmitting contact with the workpiece 38 at a remote location. The sensor 40 is operative to produce an output signal representative of received elastic waves. A pulse of electric current is applied to the coil 36 by a pulse generator 42 thereby producing pulse heating of the coil 36. The pulse heating of the coil 36 creates rapid thermal expansion and contraction of the coil 36 producing an acoustic wave coupled to the workpiece 38. Elastic waves are thereby induced in the nonconductive workpiece 38. The elastic waves impinge upon the acoustic sensor 40 and its corresponding output is applied to an amplifier 42. The amplifier output signal is displayed on an oscilloscope 44 or otherwise recorded, displayed, or subjected to analysis. The presence of a defect 46 causes a variation in the amplitude or other characteristics of the displayed output signal. The output signal may exhibit a diminished amplitude or a greater amplitude in the presence of a defect 46 depending on the nature and location of the defect 46 in the workpiece 38. The time of arrival of the elastic waves at the sensor 40 may also be affected by the presence of a defect.

Figure 3:
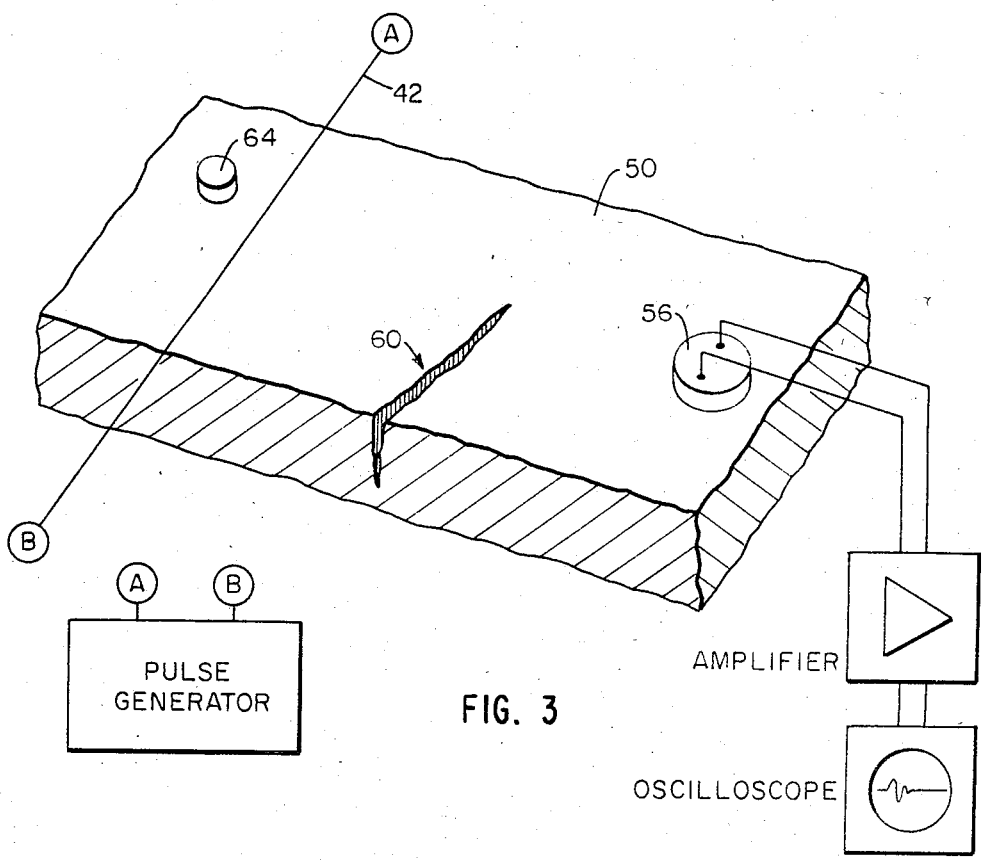
FIG. 3 shows an embodiment in accordance with the present invention in which a fine wire is bonded to a surface of a nonconductive workpiece.
Figure 4:
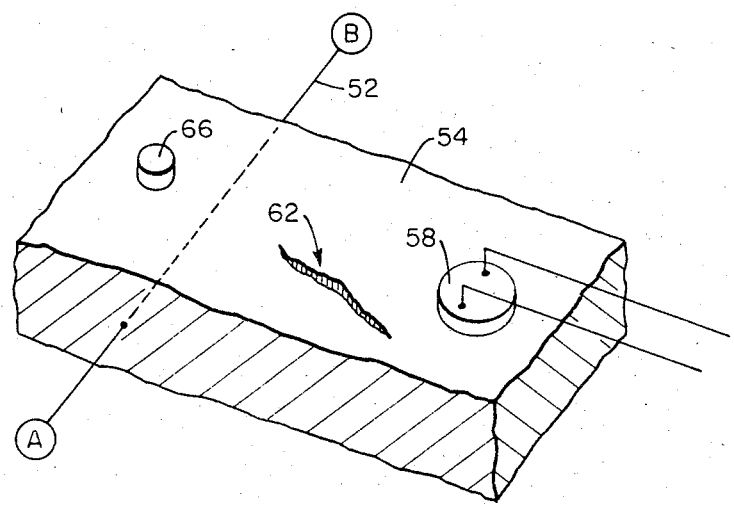
FIG. 4 illustrates an embodiment of the present invention in which a fine wire is imbedded within a workpiece in accordance with the present disclosure.

Other embodiments employed for inspection of workpieces of nonconductive material are illustrated in FIGS. 3 and 4. FIG. 3 shows a fine wire 48 bonded for acoustic coupling to a workpiece 50 of nonconductive material. FIG. 4 illustrates a fine wire 52 embedded or otherwise disposed within a nonconductive workpiece 54. A pulse of current is applied to the fine wire 48 or 52 thereby producing elastic waves in a workpiece 50 or 54 as a consequence of rapid thermal expansion and contraction of the respective wire 48 or 52 disposed in elastic wave transmitting contact with the respective workpiece. Elastic waves, thus produced, in the absence of a defect or flaw, travel through the workpiece 50 or 54 to an acoustic sensor 56 or 58 also disposed in elastic wave transmitting contact with the workpiece 50 or 54. The acoustic sensor 56 or 58 produces an output signal which is representative of received elastic waves. In the presence of a defect 60 or 62 the acoustic sensor 56 or 58 produces an output signal having an amplitude or other characteristic which varies depending upon the nature and location of the defect 60 or 62.

A magnet 64 or 66 may be disposed adjacent the fine wire 48 or 52 respectively to enhance inducement of elastic waves in the workpiece 50 or 54. Pulse energization of the wire proximate to the magnet causes a pulse vibratory displacement of the wire resulting from the interaction of the magnetic field produced by pulse current flow through the wire with the magnetic field of the magnet. This effect, known as an electrodynamic effect, causes elastic waves to be induced in the workpiece resulting from the pulse vibratory displacement of the wire disposed in elastic wave transmitting contact with the workpiece.

Elastic waves detected by an acoustic wave sensor may result from a combination of electrodynamic and thermoelastic effects.

Figure 5:
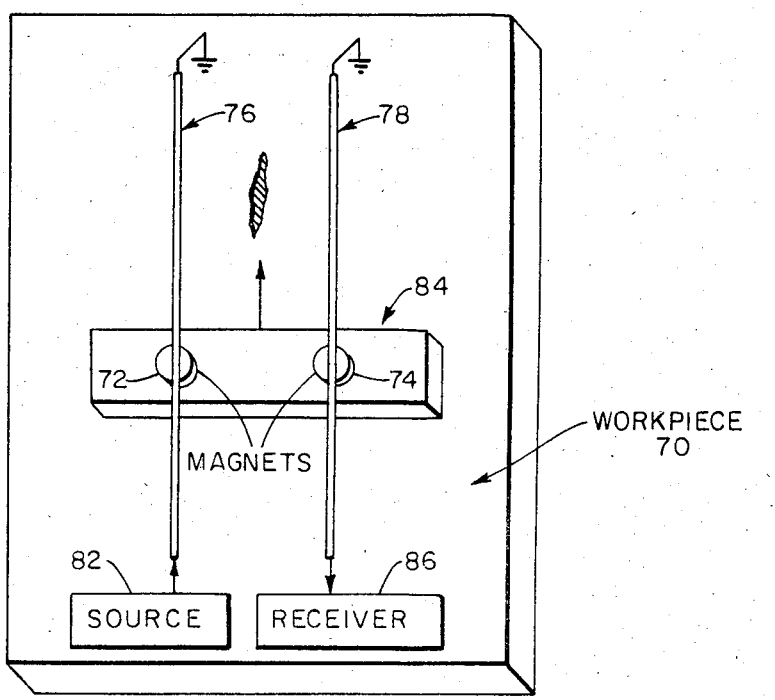
FIGS. 5 and 6 illustrate embodiments of claims 22-24.

In another embodiment of the invention illustrated in FIG. 5, a first elongated conductor 76 and a second elongated conductor 78 are disposed in mechanical contact with the workpiece 70 such that the conductors 76 and 78 are insulated from the workpiece. Magnetic field generators 72 and 74 are disposed adjacent the respective conductors. The first conductor 76 is electrically energized via source 82 to induce elastic waves in the workpiece 70 by thermoelastic or electrodynamic effect. A receiver 86 is connected to the conductor 78 and is operative to produce an output signal representative of elastic waves impinging the conductor 78 in the vicinity of the localized magnetic field generator 74. As illustrated, the magnetic field generator 72 may be employed cooperatively with conductor 76 to induce elastic waves in the workpiece electrodynamically.

Figure 6:
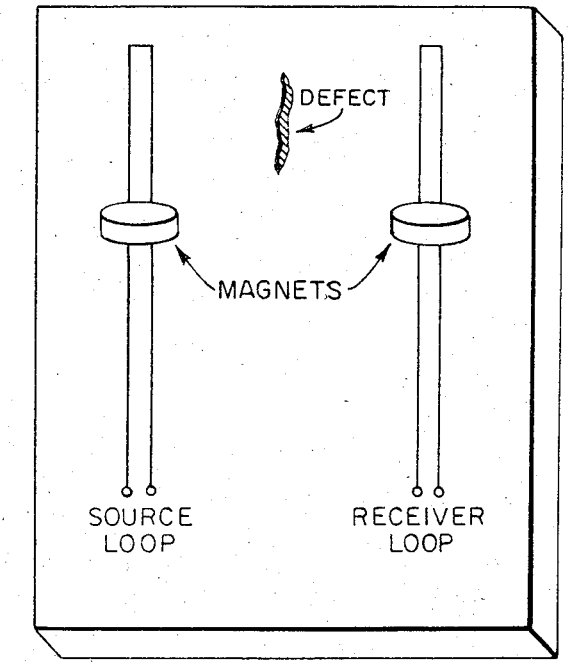

FIG. 6 illustrates an embodiment of the invention operative in the manner described with respect to FIG. 5 however the conductors corresponding to conductors 76 and 78 are formed as loops to reduce the sensitivity of the detector to electromagnetic noise.

The invention is applicable for nondestructive inspection and detection of conductive or nonconductive workpieces in accordance with the present disclosure and may be employed for inspection of materials such as graphite epoxy having directional conductivity characteristics.

The above examples and discussion are solely illustrative of methods and apparatus for practicing the disclosed invention and the scope of the invention is to be considered limited only by the following claims.

What is claimed is:

1. Apparatus for nondestructive inspection of a conductive surface of a workpiece for deep defects comprising:
   electrode means removably disposable in contact with said surface of said workpiece at a point of contact to provide at least one resistive current path between said point of contact and said surface, said means providing for electrical conduction therethrough to said surface;
   means for electrically energizing said electrode means to thermoelastically induce elastic waves in said surface proximate to said point of contact;
   electrode contacting means adapted for contacting said surface, providing for electrical conduction therethrough, and providing a path for return current from said energizing means;
   ultrasonic detection transducer means coupled to receive elastic waves impinging said means from any direction along said workpiece surface, said transducer means operative to provide an output signal having specified characteristics and representative of elastic waves induced in said workpiece surface at said electrode means, said elastic waves traversing said workpiece surface and impinging said ultrasonic detection transducer means in the absence of a defect, the presence of a defect in said surface being detectable as a variation in said transducer means output signal characteristics.

2. The apparatus of claim 1 wherein said electrode means includes a ball electrode.

3. The apparatus of claim 1 wherein said ultrasonic transducer means includes a piezoelectric transducer.

4. The apparatus of claim 1 wherein said ultrasonic transducer means includes a capacitive transducer.

5. The apparatus of claim 1 wherein said ultrasonic transducer means includes an optical transducer.

6. A method for nondestructive inspection of a conductive surface of a workpiece comprising the steps of:
   contacting said surface at a point of contact with at least one resistive point contact electrode;
   electrically energizing said surface at said point of contact to thermoelastically induce elastic waves in said surface at said point of contact;
   contacting said surface remote from said point of contact with an electrode so as to provide a path of return current through said conductive surface upon electrical energization of said point contact electrode;
   sensing elastic waves in said workpiece with an ultrasonic transducer operative to produce an output signal indicative of received elastic waves impinging said transducer from any direction along said workpiece surface, the presence of a defect in said surface being detectable as a variation in the characteristics of said transducer output signal.

7. Apparatus for nondestructive inspection of a workpiece for defects comprising:
   an electrical conductor having a predetermined length disposed in close elastic wave transmitting and electrically insulated contact with said workpiece;
   means for electrically energizing said conductor with a unitary pulse to induce waves in a volume of said workpiece by thermoelastic effect;
   ultrasonic detection transducer means coupled to receive elastic waves impinging upon said transducer means from any direction along said workpiece, said transducer operative to provide an output signal having specified characteristics which are a response to said unitary pulse;
   the presence of a defect localized to a portion of said volume in said workpiece being detectable as a variation in said output signal characteristics for said unitary pulse.

8. The apparatus of claim 7 wherein said workpiece is a cylindrical workpiece and said conductor comprises a wire coil closely wrapped on said workpiece.

9. The apparatus of claim 7 wherein said wire is disposed within said workpiece and in contact therewith.

10. The apparatus of claim 7 wherein said ultrasonic detection transducer means includes a piezoelectric transducer.

11. The apparatus of claim 7 wherein said ultrasonic detection transducer means includes an optical transducer.

12. The apparatus of claim 7 wherein said ultrasonic detection transducer means includes a capacitive transducer.

13. A method for nondestructive inspection of a workpiece for defects comprising the steps of:
   locating an electrical conductor of a predetermined length in close mechanical, electrically insulating contact with said workpiece;
   electrically energizing said conductor with a unitary pulse to induce elastic waves in a volume of said workpiece by thermoelastic effect;
   sensing elastic waves in said workpiece with an ultrasonic transducer disposed in elastic wave transmitting contact with said workpiece, said transducer providing an output signal having specified characteristics which are a function of said unitary pulse;
   analyzing said transducer output signal, the presence of a defect localized to a portion of said volume in said workpiece being detectable as a variation in said output signal characteristics for said unitary pulse.

14. Apparatus for nondestructive inspection of a workpiece comprising:
- at least one elongated electrical conductor disposed in close mechanical, electrically insulating contact with said workpiece along a specified path;
- at least one movable local magnetic field generating means disposed proximate to scan said conductor and generating at least one local magnetic field each limited to a small section of said conductor;
- means for electrically energizing said conductor and inducing elastic waves in said workpiece solely at said at least one small section electrodynamic effect;
- ultrasonic detection transducer means coupled to receive elastic waves from said workpiece, said transducer operative to provide an output signal having specified characteristics;
- the presence of a defect in said workpiece being detectable as a variation in said transducer output signal characteristics.

15. The apparatus of claim 14 including means for scanning said magnetic field generating means along a path proximate to said path of said conductor.

16. The apparatus of claim 14 wherein said magnetic field generating means includes a magnet.

17. The apparatus of claim 14 wherein said magnetic field generating means includes an electromagnet.

18. The apparatus of claim 14 wherein said ultrasonic detection transducer means includes a piezoelectric transducer.

19. The apparatus of claim 14 wherein said ultrasonic detection transducer means includes an optical transducer.

20. The apparatus of claim 14 wherein said ultrasonic detection transducer means includes a capacitive transducer.

21. A method for nondestructive inspection of a workpiece comprising the steps of:
- disposing at least one elongated conductor in close mechanical, electrically insulating contact with said workpiece along a specified path;
- scanning at least one local magnetic field generating means along said conductor;
- said magnetic field being limited to a small section of said conductor
- electrically energizing said conductor to induce elastic waves in said workpiece by electrodynamic effect solely at said small section;
- coupling elastic waves from said workpiece to an ultrasonic detection transducer operative to provide an output signal having specified characteristics;
- detecting a defect in said workpiece as a variation in said transducer output signal characteristics.

22. Apparatus for nondestructive inspection of a workpiece comprising:
- first and second substantially parallel elongated conductors, each adapted to be in close mechanical, electrically insulating contact with said workpiece;
- first means for generating a localized magnetic field disposed adjacent said second elongated conductor;
- second means for applying electrical excitation to said first elongated conductor;
- third means for scanning said first means along said second elongated conductor to detect a workpiece defect where present adjacent said second conductor.

23. Apparatus for nondestructive inspection of a workpiece comprising:
- means contacting said workpiece for generating elastic waves in said workpiece;
- at least one elongated electrical conductor having an elastic wave detecting length and adapted to be disposed in close mechanical, electrically insulating contact with said workpiece along said length;
- at least one magnetic field source providing a local magnetic field dimensionally limited to a small section of said length and adapted to scan said length;
- means for sensing an electrical signal in said at least one elongated conductor as an indication of a workpiece defect proximate to said small section.

24. The apparatus of claim 23 wherein said elastic wave generating means includes:
- at least one electrical conductor disposed in close mechanical, electrically insulating contact with said workpiece;
- means for electrically energizing said conductor; and
- a source of a magnetic field dimensionally limited to a small section of said conductor and adapted to scan there along.

* * * * *

UNITED STATES PATENT AND TRADEMARK OFFICE
CERTIFICATE OF CORRECTION

PATENT NO. : 4,593,565

DATED : June 10, 1986

INVENTOR(S) : Jacques R. Chamuel

It is certified that error appears in the above-identified patent and that said Letters Patent is hereby corrected as shown below:

Column 2, line 18, "occur. an acoustic" should read --occur. An acoustic--

Column 6, line 25, "induce waves" should read --induce elastic waves--

Signed and Sealed this

Twenty-third Day of December, 1986

Attest:

DONALD J. QUIGG

Attesting Officer     Commissioner of Patents and Trademarks